(12) United States Patent
Jones (10) Patent No.: US 10,201,397 B1
(45) Date of Patent: Feb. 12, 2019

(54) DENTAL CONTROL UNIT

(71) Applicant: Clark L Jones, Cave Creek, AZ (US)

(72) Inventor: Clark L Jones, Cave Creek, AZ (US)

( * ) Notice: Subject to any disclaimer, the term of this patent is extended or adjusted under 35 U.S.C. 154(b) by 0 days.

(21) Appl. No.: 15/732,968

(22) Filed: Jan. 19, 2018

Related U.S. Application Data

(60) Provisional application No. 62/499,200, filed on Jan. 19, 2017.

(51) Int. Cl.
*A61C 1/02* (2006.01)
*A61C 1/00* (2006.01)
*A61C 3/02* (2006.01)

(52) U.S. Cl.
CPC .......... *A61C 1/0023* (2013.01); *A61C 1/0038* (2013.01); *A61C 1/0061* (2013.01); *A61C 3/02* (2013.01)

(58) Field of Classification Search
CPC ...... A61C 1/0023; A61C 1/003; A61C 1/0038
See application file for complete search history.

(56) References Cited

U.S. PATENT DOCUMENTS

| | | | | |
|---|---|---|---|---|
| 3,296,698 A | * | 1/1967 | Staunt | A61C 1/0007 137/636.1 |
| 3,359,638 A | * | 12/1967 | Maurer | A61C 1/0023 137/636.1 |
| 3,855,704 A | * | 12/1974 | Booth | A61C 1/0023 251/63 |
| 4,676,750 A | * | 6/1987 | Mason | A61C 1/0023 433/101 |
| 5,300,926 A | * | 4/1994 | Stoeckl | A61G 15/02 345/156 |
| 6,866,507 B2 | * | 3/2005 | Beerstecher | A61C 1/0023 200/86.5 |

* cited by examiner

*Primary Examiner* — Ralph Lewis
(74) *Attorney, Agent, or Firm* — Tod R. Nissle, P.C.

(57) ABSTRACT

A foot control unit enables a dentist to operate a dental hand piece using the dentist's knowledge of selected positions of the control unit, along with the ability of the dentist to feel when the control unit is in a selected position.

1 Claim, 11 Drawing Sheets

DENTAL CONTROL UNIT

This application claims priority based on Provisional Patent Application Ser. No. 62/499,200 filed Jan. 19, 2017.

This invention relates to control units.

More particularly, the invention relates to a dental control unit.

Those of skill in the art have for many years endeavored to provide improved control units in the dental and other fields.

Accordingly, it would be highly desirable to provide an improved dental control unit.

Therefore, it is an object of the instant invention to provide an improved dental control unit.

This, and other and further objects of the instant invention will be apparent to those skilled in the art from the following detailed description thereof, taken in conjunction with the drawings, in which:

FIG. 37 is a perspective view illustrating the contact between the ganged cam plates of the foot control module and the valves of the valve control module;

FIG. 38 is a front perspective view further illustrating the contact between the ganged cam plates of the foot control module and the valves of the valve control module; and, FIG. 39 is a perspective view further illustrating the contact between the ganged cam plates of the foot control module and the valves of the valve control module.

Briefly, provided are improvements in dental apparatus. The dental apparatus comprises at least one dental high speed hand piece including at least one rotatable drill bit. The drill bit has at least two operative positions, a primary on operative position in which said drill bit is activated and is rotating, and, a secondary off operative position in which the drill bit is deactivated and is stationary. The dental apparatus also includes at least a first control line to deliver pressurized water to the dental hand piece; at least a second control line to deliver compressed air to the dental hand piece; and, at least a third control line to supply turbine drive air that will activate and deactivate the drill bit. The improvements in the dental apparatus comprise a dental control unit to operate the first, second, and third control lines. The improvements comprise a housing positioned on a floor; a generally horizontally oriented plate pivotally mounted on said housing to be laterally displaceable through an arc by engaging the plate with a foot and pivoting the foot and the plate simultaneously through an arc; a plurality of horizontally oriented cam edges connected to the plate to move simultaneously with the plate; and, a plurality of actuable valves fixedly mounted on the housing and operatively associated with the cam edges and the first, second and third control lines. The plate and cam edges are simultaneously displaceable through at least five operative positions to actuate periodically selected ones of the valves. The operative positions include a first operative position in which the drill bit is activated and pressurized water is delivered to the hand piece; a second operative position in which the drill bit is activated and compressed air is delivered to the hand piece; a third operative position in which the drill bit is deactivated, compressed air is not delivered to the hand piece, and pressurized water is not delivered to the hand piece; a fourth operative position in which the drill bit is deactivated and compressed air is delivered to the hand piece; and, a fifth operative position in which the drill bit is deactivated and pressurized water and compressed air together are delivered to the hand piece. These latter two functions are new and were not possible with previous foot control devices.

Turning now to the drawings, which depict the presently preferred embodiments of the invention for the purpose of illustration, and not limitation, of the invention, FIGS. 1 to 37 illustrate a dental control unit constructed in accordance with the principles of the invention and generally indicated by reference character 10. At the outset of the development of the dental control unit 10 of the invention, the initial focus was on improving a conventional dental foot control unit which included a separate water control switch that had to be activated or deactivated by the dentist's foot during operation of the foot control apparatus to select between the "cut wet" and "cut dry" functions of the drill. Over many months, the conventional control unit morphed into dental control unit 10 with two additional functions that were not previously possible. Unexpected discoveries and advantages of the invention are set forth below.

Dental control unit 10 is designed to be retrofit to a conventional dental station. As is well known, a conventional dental station includes at least one hand piece with a rotatable drill bit and a pneumatically driven turbine that rotates the drill bit. A first line leading into the dental station provides compressed air coolant to the hand piece; a second line leading into the dental station provides air pressure to activate the water coolant solenoid valve that provides water under pressure to the hand piece; and, a third line leading into the dental station provides compressed air to drive the turbine that rotates the drill bit. A fourth line leads out of the dental station to supply compressed air to the three valves of the dental control unit 10.

Figure 1:
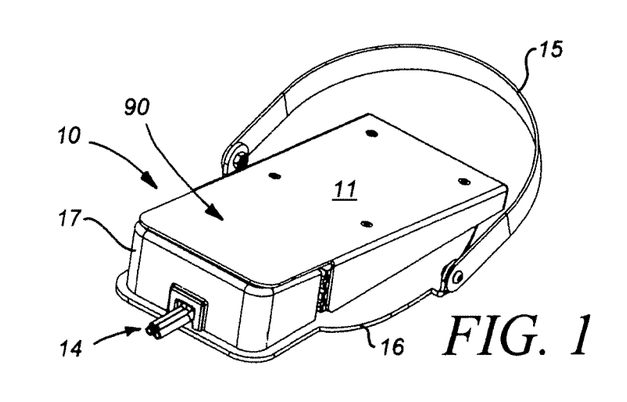
FIG. 1 is a perspective view illustrating a dental control unit constructed in accordance with the principles of the invention and with the foot control module in the centered, or neutral position.
Figure 2:
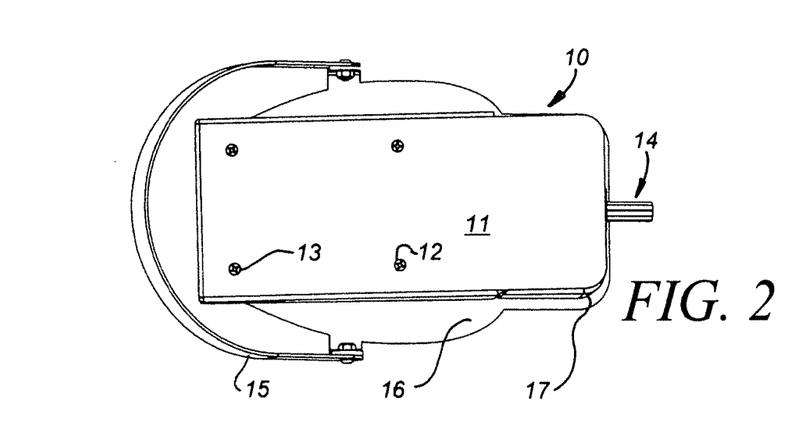
FIG. 2 is a top view of the dental control unit of FIG. 1 illustrating additional construction details thereof.
Figure 3:
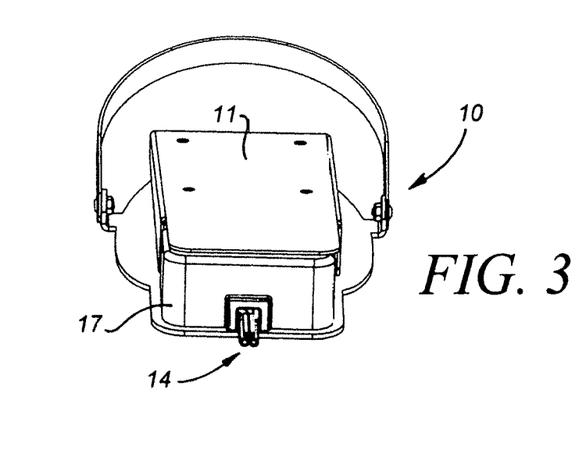
FIG. 3 is a front view of the dental control unit of FIG. 1 illustrating additional construction details thereof.
Figure 4:
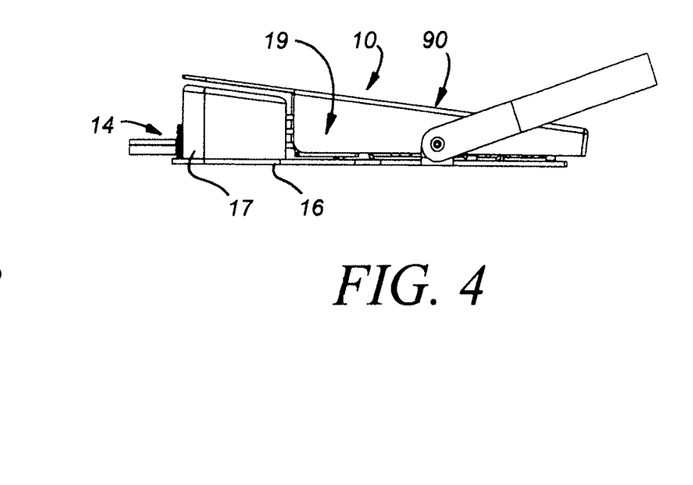
FIG. 4 is a side view of the dental control unit of FIG. 1 illustrating additional construction details thereof.
Figures 5, 8:
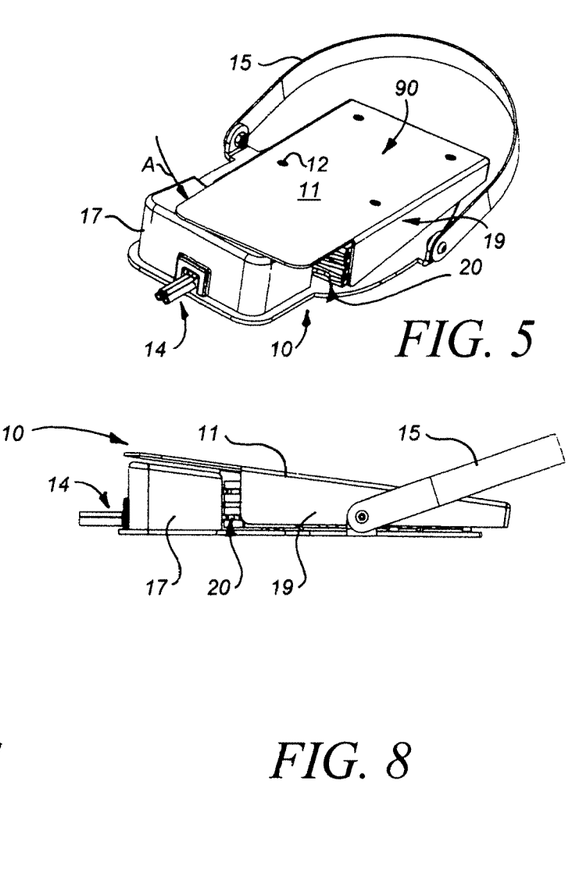
FIG. 5 is a view of the dental control unit of FIG. 1 with the foot control module laterally displaced through an arc to the left in the direction of arrow A.
FIG. 8 is a side view of the dental control unit of FIG. 5 illustrating further construction details thereof.
Figure 6:
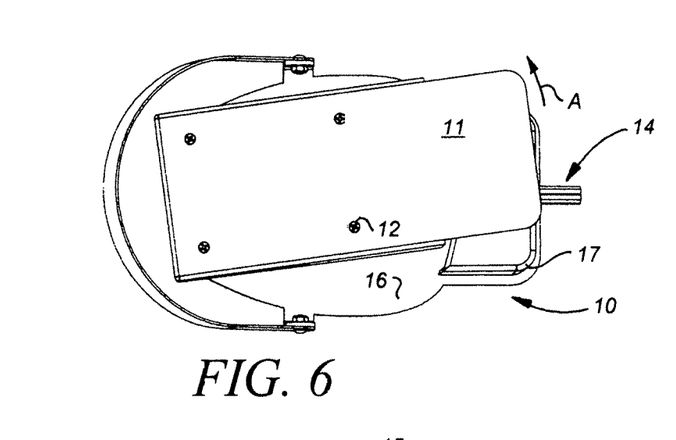
FIG. 6 is a top view of the dental control unit of FIG. 5 illustrating further construction details thereof.
Figure 7:
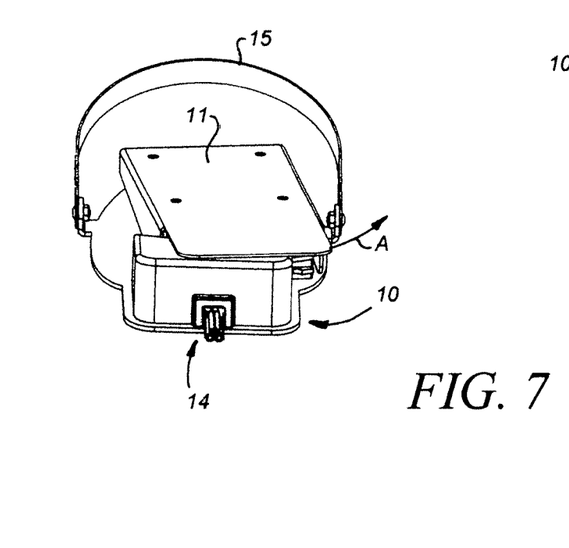
FIG. 7 is a front view of the dental control unit of FIG. 5 illustrating further construction details thereof.
Figure 13:
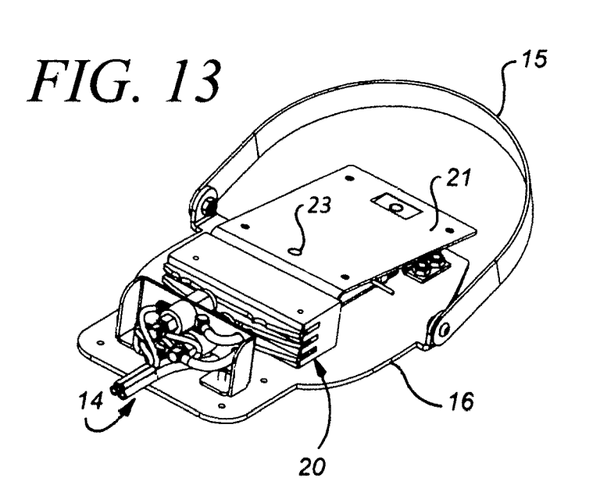
FIG. 13 is a perspective view of the dental control unit of FIG. 1 with the foot control plate and valve control module cover removed.
Figure 14:
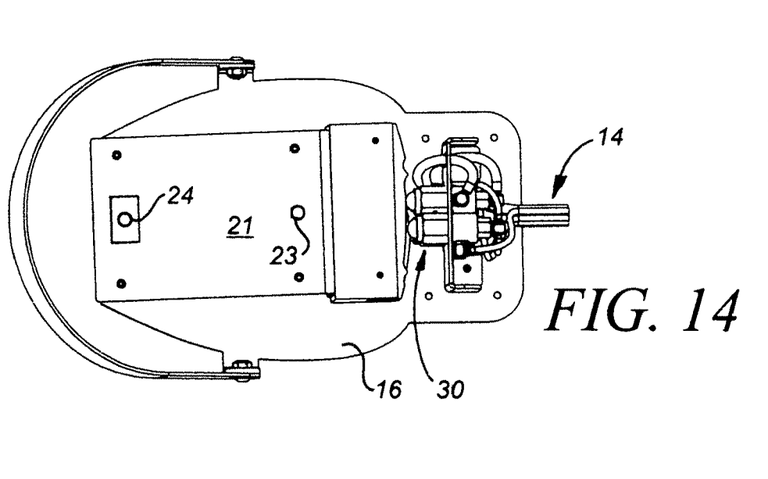
FIG. 14 is a top view of the dental control unit of FIG. 13 illustrating further construction details thereof.
Figure 15:
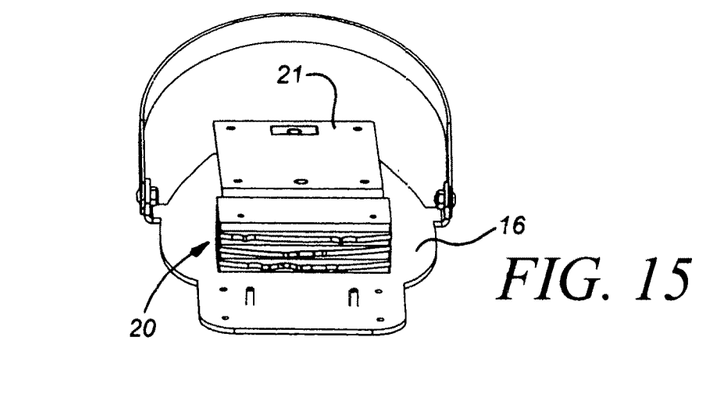
FIG. 15 is a front view of the dental control unit of FIG. 13 illustrating further construction details thereof.
Figure 16:
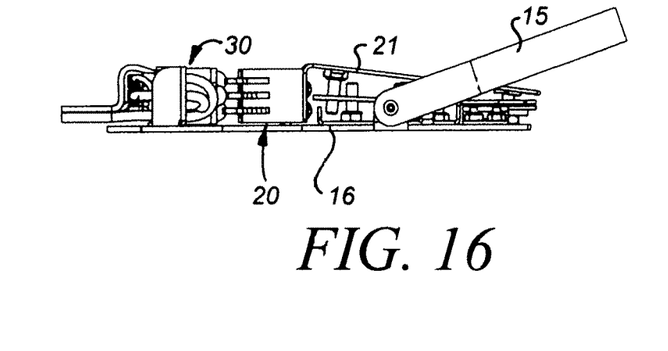
FIG. 16 is a side view of the dental control unit of FIG. 13 illustrating further construction details thereof.
Figure 17:
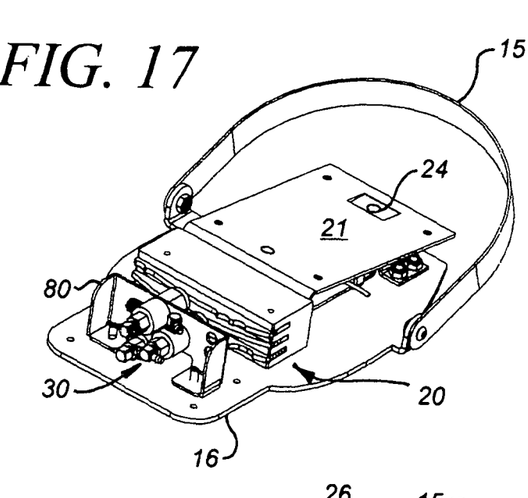
FIG. 17 is a perspective view of the dental control unit of FIG. 13 with the input and output lines in the valve assembly removed to better illustrate the construction thereof.
Figure 18:
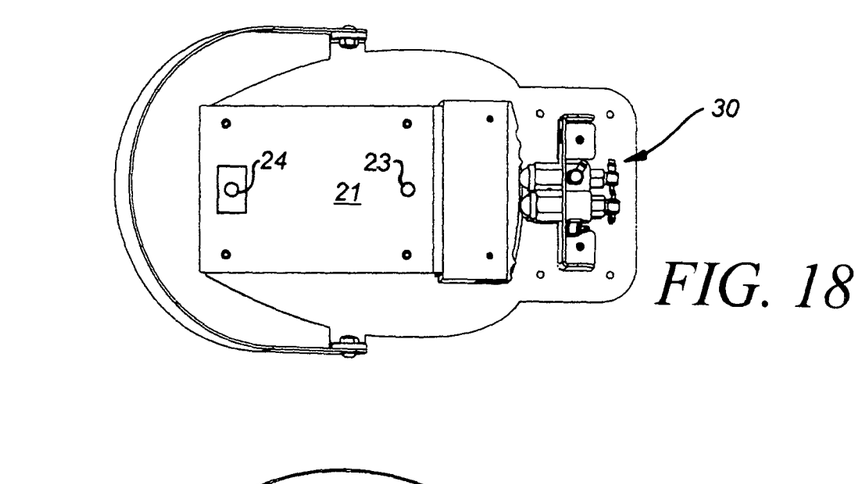
FIG. 18 is a top view of the dental control unit of FIG. 17 illustrating further construction details thereof.
Figure 19:
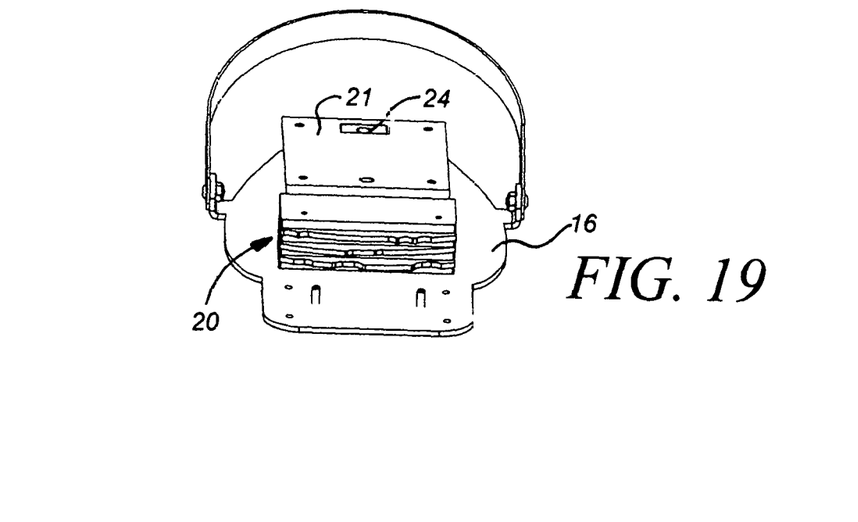
FIG. 19 is a front view of the dental control unit of FIG. 17 illustrating further construction details thereof.
Figure 20:
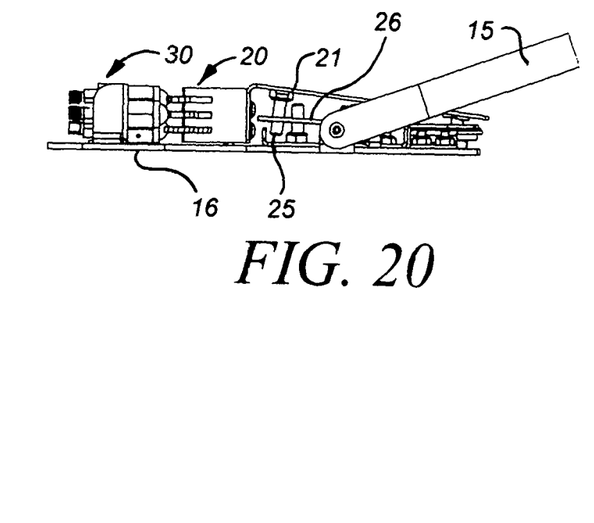
FIG. 20 is a side view of the dental control unit of FIG. 17 illustrating further construction details thereof.

In FIG. 1, dental control unit 10 includes foot control module 90, foot plate 11, and cover 17. Cover 17 encloses valve control module 30 (FIG. 14). Control line bundle 14 extends outwardly from cover 17. Foot control module 90, valve control module 30, and other components of dental control unit 10 are mounted on base plate 16. Screws 12, 13 or other fasteners are used to secure foot plate 11 to sub-plate 21 (FIG. 13). In FIGS. 1 to 4, foot plate 11 is in a centered, neutral position. During use of dental control unit 10, a dentist places on plate 11 one of the shoes (not shown) he is wearing. The toe of the shoe (and toes of the dentist's foot) points toward control line bundle 14. The dentist presses his foot against plate 11 and then turns his foot—and therefore his shoe—laterally to the left or right to pivot simultaneously plate 11 through an arc with his foot. For example, in FIGS. 5 to 8, foot plate 11 has been laterally pivoted from the neutral position to the left in the direction of arrow A. And, in FIGS. 9 to 12, foot plate 11 has been laterally pivoted from the neutral position to the right in the direction of arrow B.

Although the arc through which plate 11 rotates can vary as desired, plate 11 currently laterally rotates to the left about twelve degrees from the neutral position and to the right about twelve degrees from the neutral position. Plate 11 can have an anti-slip surface.

Arcuate hoop or bail 15 is pivotally connected to base plate 16 and, when a dentist places his foot on plate 11, can be used to move dental control unit 10. In order to move dental control unit 10, the dentist lifts his foot upwardly off plate 11 until his shoe contacts and lifts hoop 15. Lifting hoop 15 also lifts the other portions of dental control unit 10 so that dental control unit 10 can, by moving the dentist's foot to the left or right, be moved to the left or to the right, as desired.

In FIGS. 13 to 16, the foot plate 11 has been removed from foot control module 90, exposing sub-plate 21. Similarly, cover 17 has been removed from over valve control module 30, exposing valve control module 30.

In FIGS. 17 to 20, control line bundle 14 is deleted to better illustrate valve control module 30, and its interaction with the ganged stack of cams mounted in cam block assembly module 20. Valve control module 30 includes bracket 80 on which three spring loaded pneumatic control valves 51, 52, and 53 (FIGS. 31 and 32) are fixedly mounted and through bracket 80 are fixedly attached to the baseplate 16.

Figure 9:
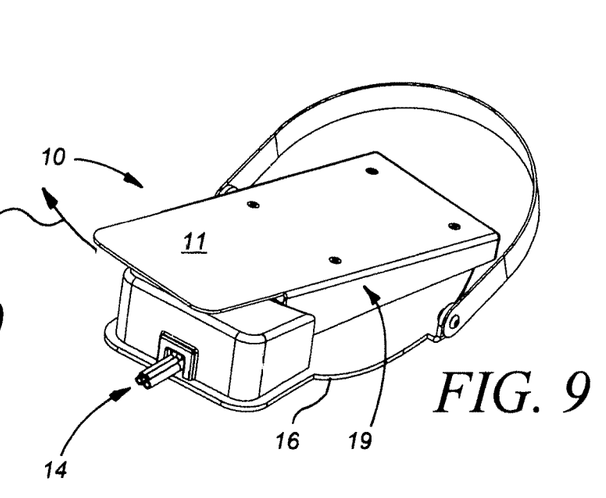
FIG. 9 is a perspective view of the dental control unit of FIG. 1 with the foot control module laterally displaced through an arc to the right in the direction of arrow B.
Figure 10:
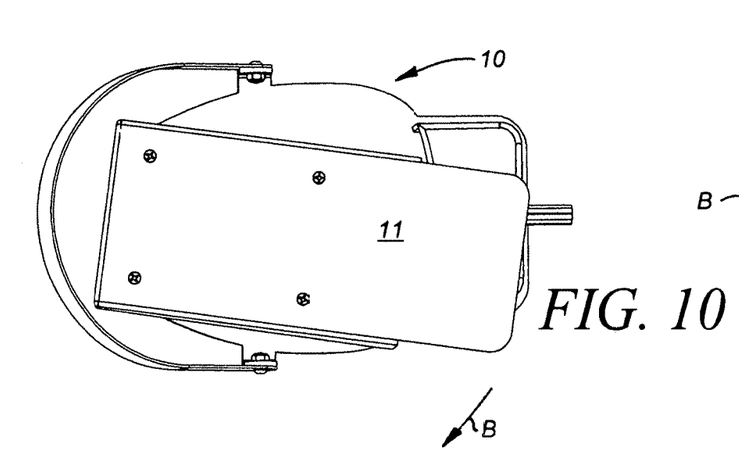
FIG. 10 is a top view of the dental control unit of FIG. 9 illustrating further construction details thereof.
Figure 11:
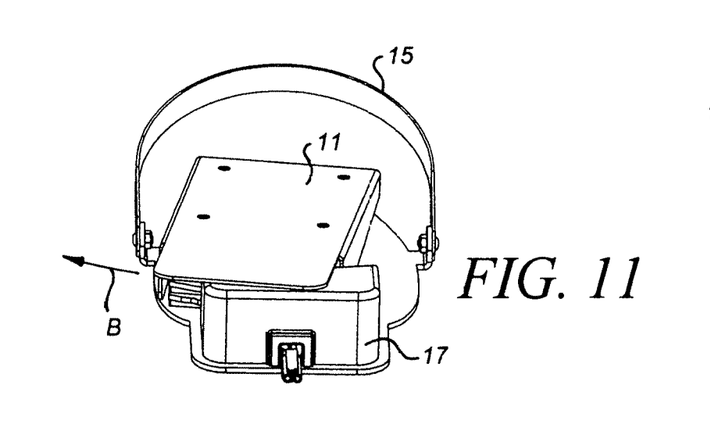
FIG. 11 is a front view of the dental control unit of FIG. 9 illustrating further construction details thereof.
Figure 12:
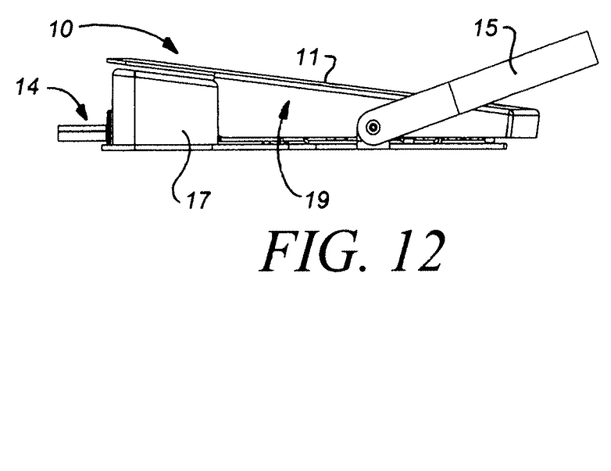
FIG. 12 is a side view of the dental control unit of FIG. 9 illustrating further construction details thereof.
Figures 21, 22, 23, 24:
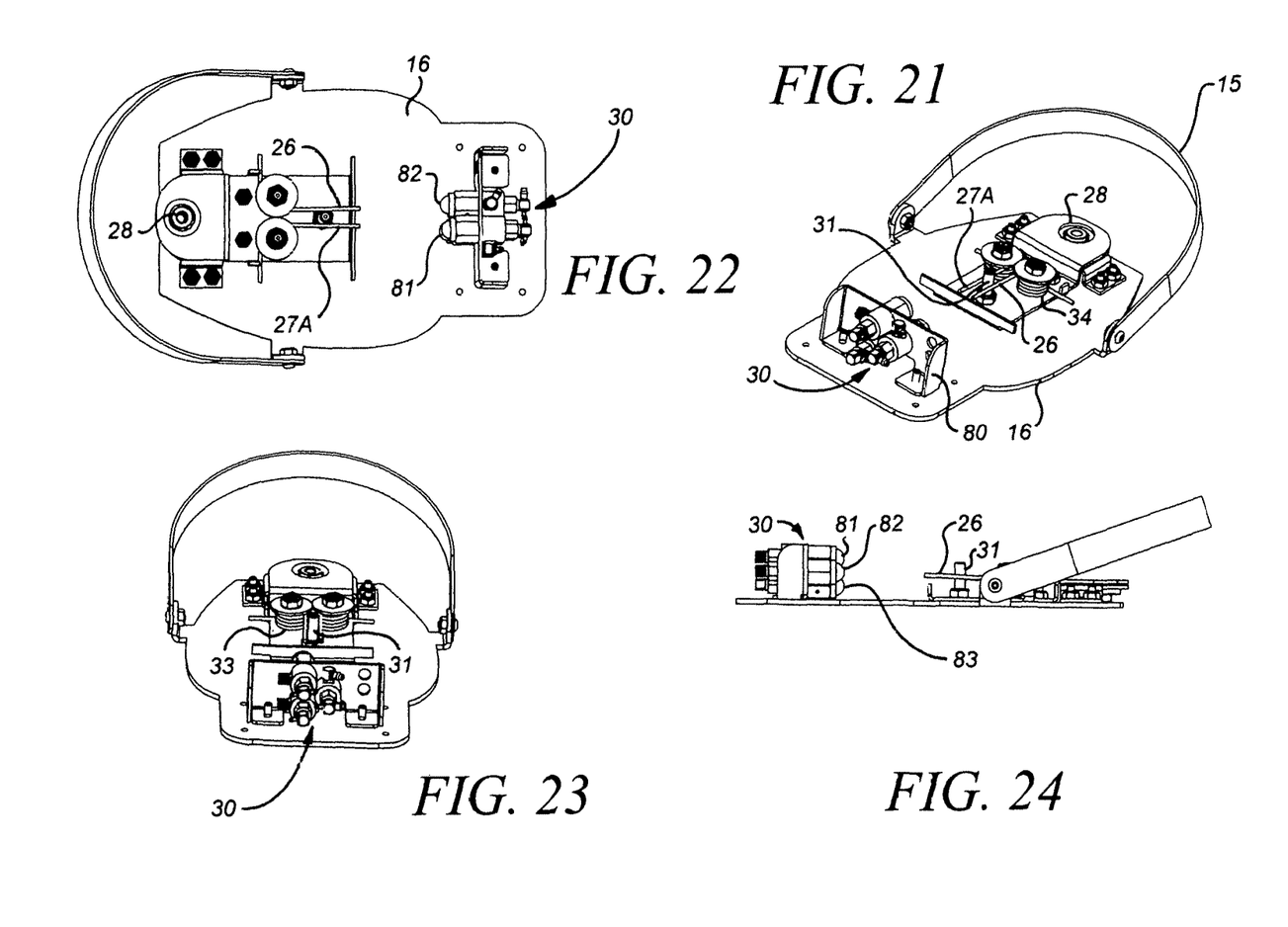
FIG. 21 is a perspective view illustrating the dental control unit of FIG. 17 with the foot control module removed.
FIG. 22 is a top view of the dental control unit of FIG. 21 illustrating further construction details thereof.
FIG. 23 is a top view of the dental control unit of FIG. 21 illustrating further construction details thereof.
FIG. 24 is a side view of the dental control unit of FIG. 21 illustrating further construction details thereof.

In FIGS. 21 to 24, the remainder of the foot control module 90 has been removed to expose the portions of dental control unit 10 on which foot control module 90 is mounted. As will be discussed further below, torsion springs 33 (FIG. 23) and 34 (FIG. 21) include arms 27A and 26, respectively, which tend to return the foot control module 90 back to the neutral position after module 90 is laterally displaced to the left in the direction of arrow A (FIG. 6) or to the right in the direction of arrow B (FIG. 9). Post 27 (FIG. 28) depends and extends downwardly from sub-plate 21. Post 27 is, when foot control module 90 is mounted as shown in FIG. 1, rotatably received by aperture 28 (FIG. 21). When foot control module 90 is laterally displaced from the neutral position to the left or right, post 27 rotates laterally in aperture 28.

As is illustrated in FIGS. 21 to 24, each spring loaded pneumatic control valve 51, 52, 53 has an actuating ball bearing 81, 82, 83 (FIG. 24), respectively, which rides along the edge of an associated cam plate 40, 41, 42 (FIG. 28), respectively, in cam block assembly module 20. Peaks 44 and valleys or detents 43 or other shapes and dimensions in the cam plates depress or release the actuating ball bearings 81 to 83 to open or close spring loaded pneumatic valves 51 to 53.

Figure 26:
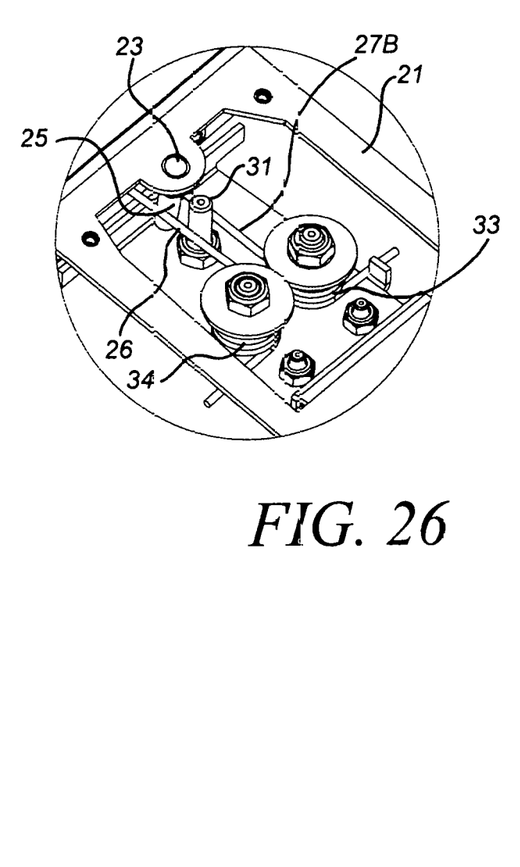
FIG. 26 is an enlarged perspective view of a section of the foot control unit of FIG. 25 illustrating further construction details thereof.
Figure 27:
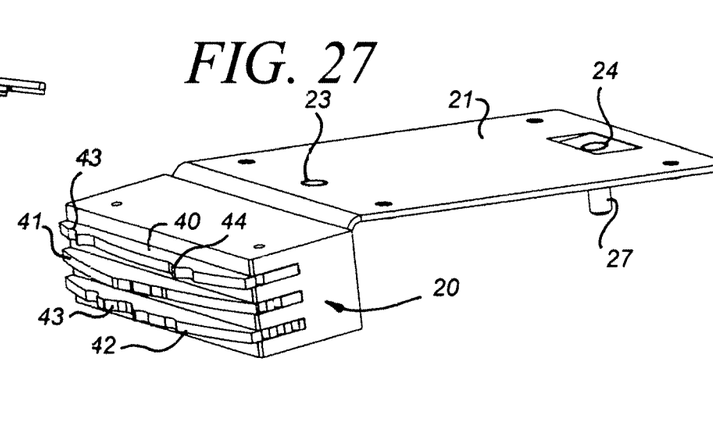
FIG. 27 is a perspective view illustrating a portion of the foot control module.
Figure 28:
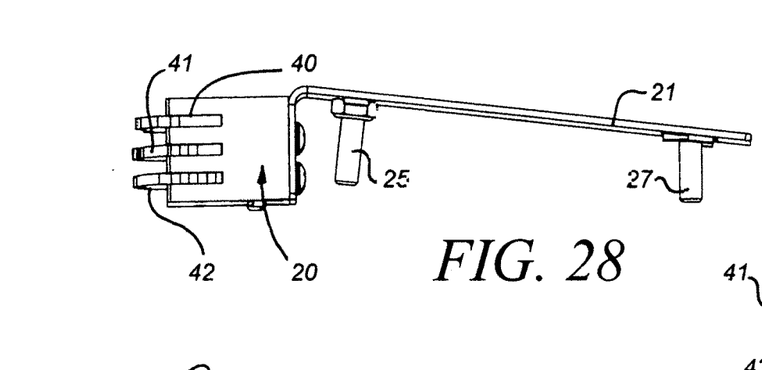
FIG. 28 is a side view of the portion of the foot control module of FIG. 27 illustrating further construction details thereof.
Figure 29:
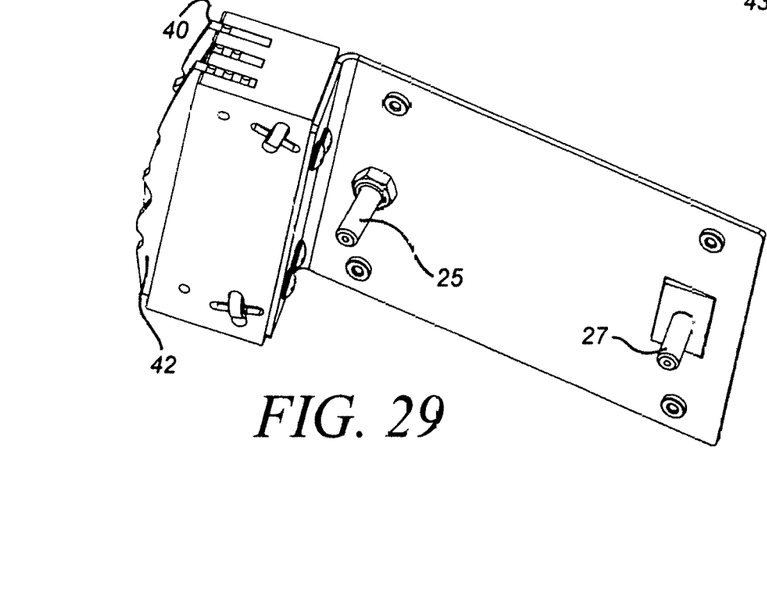
FIG. 29 is a bottom view of the portion of the foot control module of FIG. 27 illustrating further construction details thereof.
Figure 30:
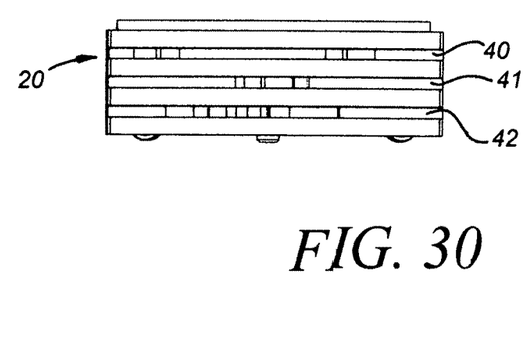
FIG. 30 is a front view of the portion of the foot control module of FIG. 27 illustrating further construction details thereof.

When control unit 10 is assembled in the manner depicted in FIG. 1, post 25 (FIGS. 28 and 29) extends downwardly intermediate arms 26 and 27A in the manner shown in FIG. 26. Fixed upstanding post 31 (FIG. 26) also extends upwardly intermediate arms 26 and 27A. When foot plate 11 and sub-plate 21 laterally pivot to the right in the direction of arrow B (FIG. 9), spring 27A is displaced and further tensioned and, consequently, generates a force which acts to move foot plate and cam block assembly module 20 back to the neutral position. When foot plate 11 and sub-plate 21 laterally pivot and move to the left in the direction of arrow A (FIG. 5), spring 26 is displaced and further tensioned and, consequently, generates a force which acts to move foot plate and cam block assembly module 20 back to the neutral position. As noted, post 27 (FIG. 28) pivots laterally in aperture 28 (FIG. 21) when foot plate and cam block assembly module 20 is laterally displaced from the neutral position to the left or right.

Figure 25:
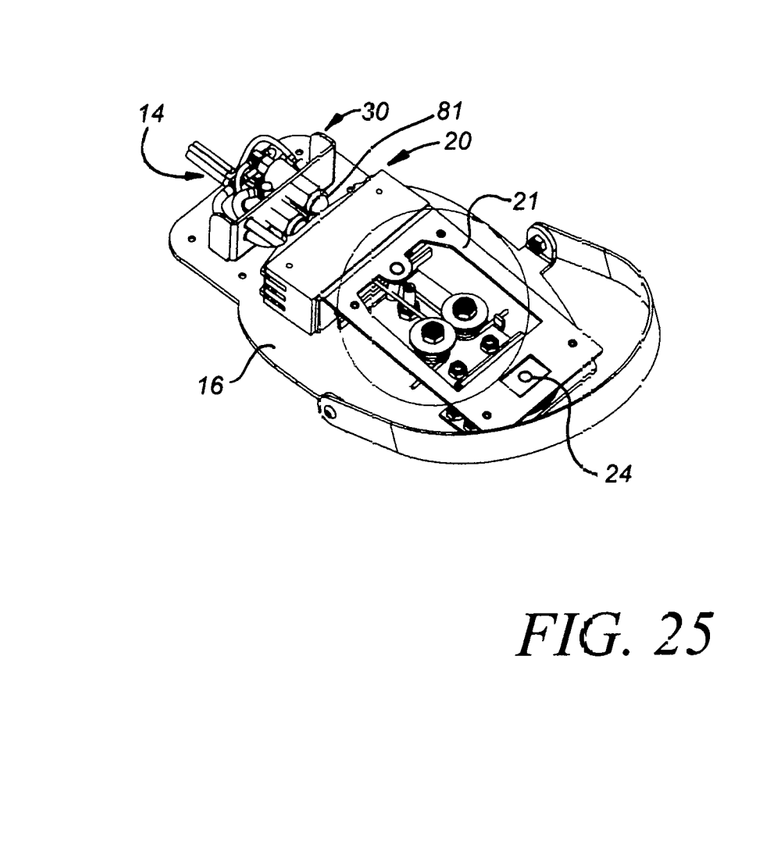
FIG. 25 is a perspective view of the foot control unit of FIG. 17 with a portion of the foot control module cut away to expose torsion springs which oppose lateral movement of the foot control module to the left or right of its centered neutral position.

In FIGS. 25 and 26, a portion of sub-plate 21 is cut away to expose and better illustrate the functioning of torsion springs 33 and 34.

The fixed attachment of cam block assembly module 20 to sub-plate 21 is illustrated in FIGS. 27 to 30.

Figures 31, 32:
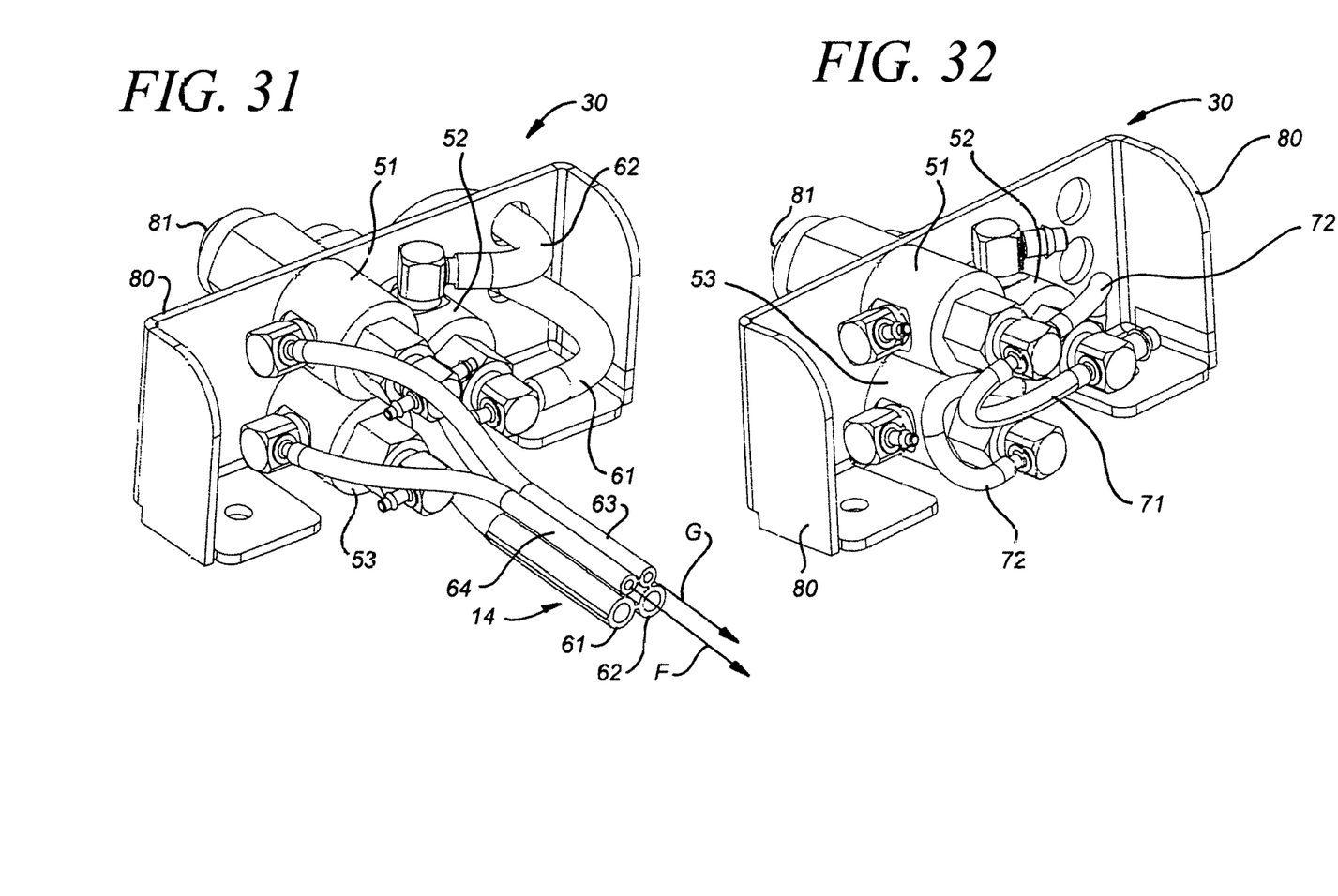
FIG. 31 is a perspective view illustrating the valve module with its output and input lines and omitting the lines that carry incoming compressed air from valve 52 to valves 51 and 53.
FIG. 32 is a perspective view illustrating the valve module without its output and input lines and including the lines that carry incoming compressed air from valve 52 to valves 51 and 53.
Figure 33:
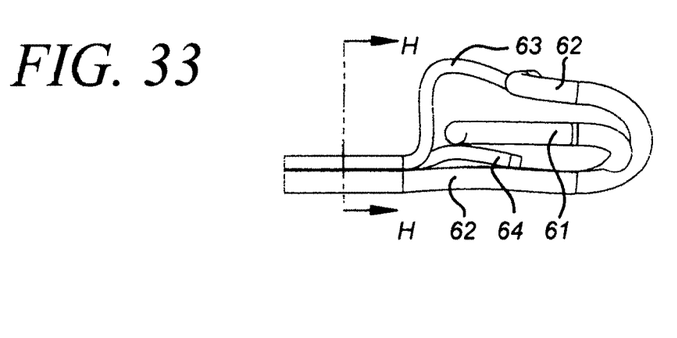
FIG. 33 is a side view illustrating the output and input lines of the valve module.
Figure 34:
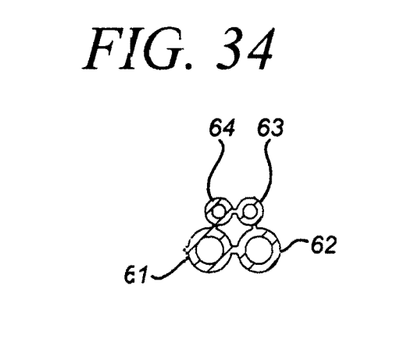
FIG. 34 is a section view further illustrating the output and input lines of the valve module and taken along section lines H-H in FIG. 33.
Figure 35:
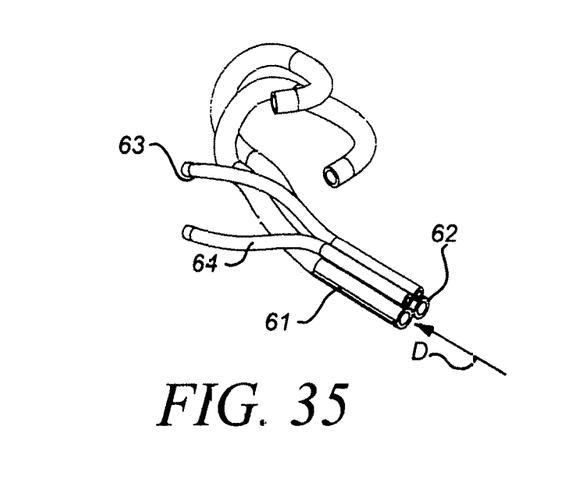
FIG. 35 is a perspective view further illustrating the output and input lines of FIG. 33.
Figure 36:
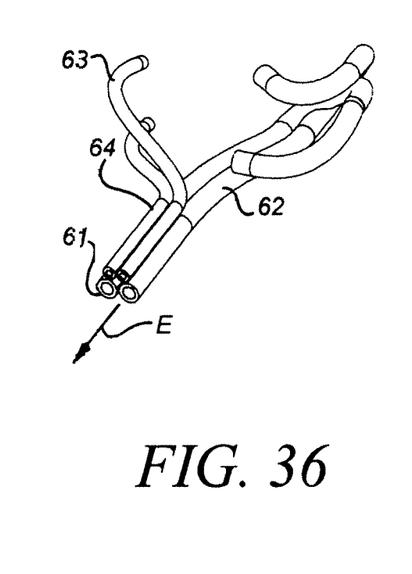
FIG. 36 is a perspective view further illustrating the output and input lines of FIG. 33.

FIG. 31 is a perspective view illustrating the valve module 30 with its hollow output and input lines, or tubing, and omitting the lines that carry incoming pressurized air from valve 52 to valves 51 and 53. Valve tubing bundle 14 is connected to a comparable four (4) line tubing bundle (not shown) In a dental station. This permits dental control unit 10 to be readily retrofitted to a dental station by simply connecting each line in bundle 14 to a comparable line in the dental station. Accordingly, line 61 is connected to a line in the dental station which carries compressed air from a dental station to valve module 30; line 62 carries compressed air from valve 52 (when valve 52 is open) to a line in the dental station which provides compressed air to drive the turbine in the hand piece which turns a drill bit in the hand piece; line 63 carries compressed air from valve 51 (when valve 51 is open) to a pneumatically controlled solenoid switch in the dental station which provides water to the hand piece in the dental station; and, line 64 carries compressed cooling air from valve 53 (when valve 53 is open) to a line in the dental station which provides cooling or drying air to the hand piece in the dental station.

Compressed air flowing through line 63 travels in the direction of arrow G in FIG. 31. Compressed air flowing through line 64 travels in the direction of arrow F in FIG. 31. Compressed air traveling through line 62 travels in the direction of arrow E in FIG. 36. Compressed air traveling through line 61 from the dental station travels in the direction of arrow D in FIG. 35.

FIG. 32 is a perspective view illustrating the valve module without its output and input lines and including the hollow lines, or tubing, that carry incoming pressurized air from valve 52 to valves 51 and 53. Hollow line 71 carries pressurized air from valve 52 to valve 51. Hollow line 72 carries pressurized air from valve 51 to valve 53

Valve 51 is a three-way valve. It exhausts air in the hollow cylindrical line or tubing 63 when it closes so that the air pressure operated solenoid valve for water in the dental station can close and stop of flow of water to the hand piece (drill) in the dental station. Valve 53 is a two-way valve that is an on-off valve that controls the flow of compressed air to the hand piece in the dental station. The flow of compressed air through valve 53 is limited by the smaller diameter of hollow cylindrical line 64. While this diameter can vary as desired, it presently is about one-sixteenth of an inch. Valve 52 is also a two-way valve that is an on-off valve that controls the compressed air that flows through hollow cylindrical fine 62 to drive the turbine which rotates the drill bit in the dental hand piece. While the diameter of line 62 (and lines 63 and 64) can vary as desired, it is presently about one-eighth of an inch. Cam 41 is shaped and dimensioned such that when valve 52 is open, it is completely, and not partially, opened; this so that the flow of drive air to the hand piece turbine is not reduced.

Figures 37, 38, 39:
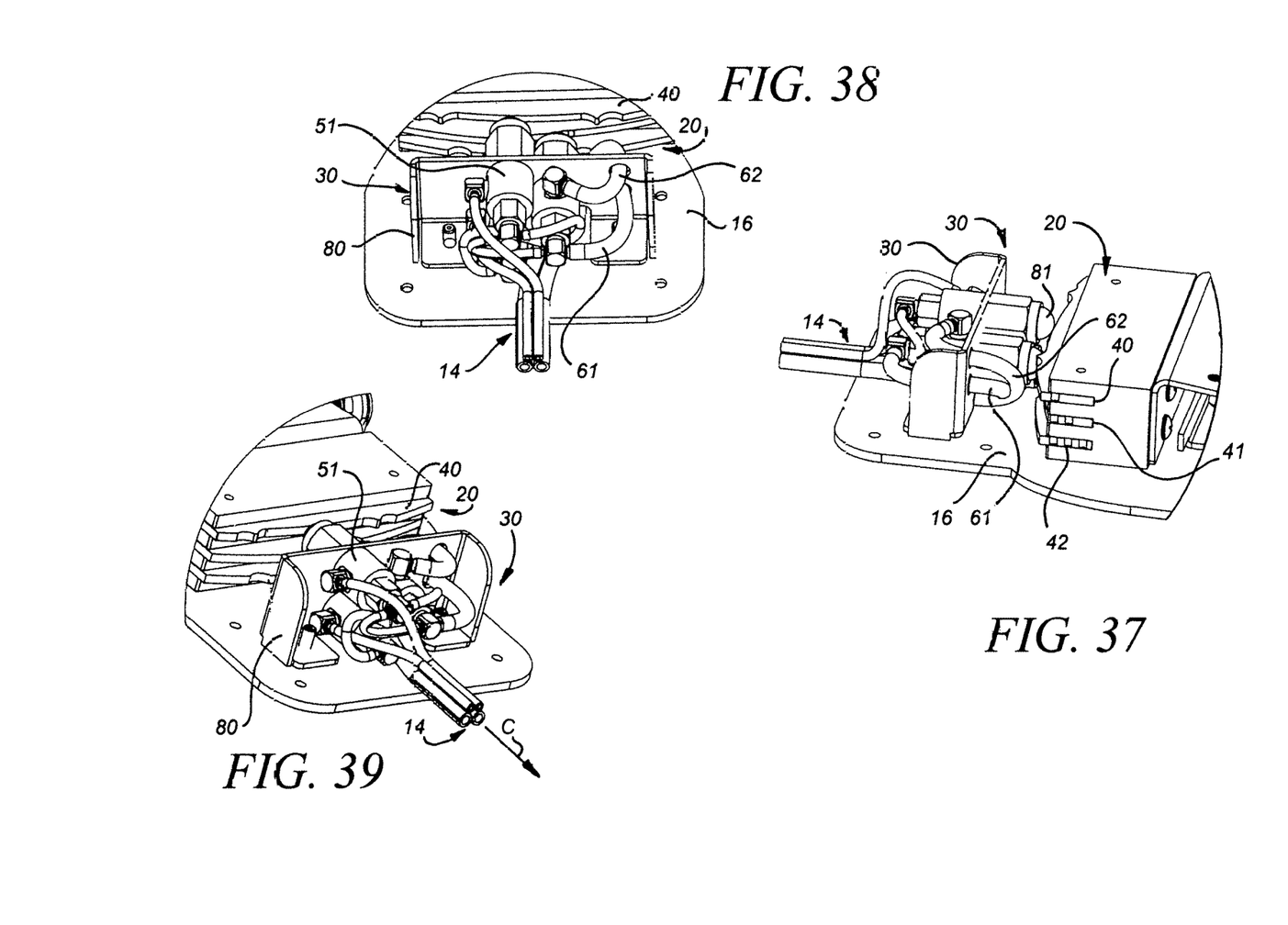

FIGS. 37 to 39 illustrate the contact between the depressible ball bearing actuators of the fixed spring loaded valves 51, 52, 53 and the contoured edges of cam plates 40, 41, and 42.

An important function of the dental control unit 10 of the invention is that, by a single movement of the foot plate, the spring loaded pneumatic valves 51, 52, 53 are gang switched as a group to achieve easily selectable combinations of valve settings that produce the necessary output functions at the hand piece of a dental station. These desired functions now include the two new functions of dispensing air alone to dry the tooth or air-water spray to wash the tooth, both without the drill rotating. These two new functions are achieved by using a ganged stack of cam plates 40, 41, 42 that can simultaneously open or close any or all of the three spring loaded pneumatic valves 51, 52, 53 as a group to obtain the desired combinations of valve settings to produce the selected output functions at the hand piece of the dental station.

The unforeseen multiplier effect of a single movement of cam block assembly module 20 gang switching the on-off states of three valves simultaneously made it possible to achieve the correct combinations of valve settings to control all five of these selectable functional positions with a single foot operated switch plate.

Another important feature of the dental control unit 10 of the invention is that the neutral position (shown in FIG. 1) of the foot control module 90 is at the center of the arc of movement of module 90 and is not at the limit of travel of module 90 to the left or right. Placing the neutral position of foot control module 90 in the center of the arc of movement enables the desired functions to be made more easily selectable by their being divided into smaller groups and placed on either side of the neutral position of foot control module 90. For example: the drill is rotating on all functions to the left of neutral and the drill is not rotating on all functions to the right of neutral. The functions to the left and right of neutral are further subdivided into wet or dry functions.

A further important feature of the dental control unit 10 of the invention is that a dentist can use a single footplate switch to control the functions of "cut wet" or "cut dry", the speed of the drill bit, the flow of water to the hand piece (either on or off), and the flow of cooling air to the hand piece (either on or off), without taking his eyes off the field of work in a patient's mouth. The dentist simply relies on the lateral rotation with his foot of the foot control module 90 into and/or through various zones. Further, the dentist relies on his knowledge of the locations of various zones of function on the arc of movement as well as on the feel of the variable rotational resistance of the control module 90 to his foot movement. As a result of this positional knowledge and variable rotational resistance feedback together, he does not need to actually look at foot control module 90 to select a particular function. This is important because it helps avoid any diversion of his attention away from the work field and expedites the progress of his work Still another important feature of the dental control unit 10 of the invention is that a dentist can readily feel when module 90 is in various desired positions of the foot control module 90. First, when the dentist uses his foot to move module 90 to the right or left of the neutral position, torsion springs 33 and 34 produce resistance which the dentist can feel. Second, when module 90 reaches the limit of its travel to the right or left, it reaches a stop and can move no further. The dentist can readily feel when module 90 reaches such a stop. Third, when a spherical ball bearing actuator of spring loaded valve 51, 52, 53 moves along the edge of a cam plate and up and over a peak 44 or into a detent 43, this changes the force required by a dentist to overcome rotational resistance and move module 90 to the left or right. In the practice of the invention, it is preferred that a dentist can readily feel this change in rotational resistance. For example, if a spring loaded spherical ball bearing actuator 81, 82, 83 drops into a detent 43, the dentist can feel the increase in rotational resistance because the dentist's foot and leg must generate more force to move module 90. The shape and dimension of the edges of the ganged stack of cam plates 40, 41, 42 can be varied as desired, but an important objective of the invention is to configure the cam edges such that a dentist can feel changes in rotational resistance when the module 90 is pivoted to desired positions or is pivoting through desired zones.

As would be appreciated by those of skill in the art, each pneumatic valve 51, 52, 53 is opened—or activated—by depressing the spring loaded valve's spherical ball bearing actuator to depress the plunger of the valve. Cam plates 40, 41, 42 are configured to accomplish this function, in conjunction with valves 51-53, by producing compressive forces on the spherical ball bearing actuator of each valve 51-53. The compressive forces depress each spring loaded valve's spherical ball bearing actuator from its normally off operative position. This actuator ball movement opens the correct valve or valves. When the compressive force on a spring loaded valve's ball bearing actuator 81, 82, 83 (FIG. 24) is released, the ball bearing actuator returns to its normally off operative position and the valve closes.

Another important feature of the invention is that a valve 51, 52, 53 can remain "on" or open while foot control module 90 is pivoted from the neutral position through a selected distance or zone (i.e., is pivoted through an arc having a selected length). This enables—as earlier described—the cam—valve system of the invention to gang activate simultaneously the required valves that control the desired functions of the dental hand piece (drill) through a dental station. For example, a drill bit can be rotated simultaneously with water and/or air being directed to the drill or hand piece by a dental station. By using the single rotatable foot plate control as a function selector switch the dental station can now also direct and supply the hand piece to dispense dry air alone without the drill rotating or to dispense combined air water spray without the drill rotating which are new functions not previously available from the hand piece.

A further important feature of the invention is that the single footplate selector switch function of dental control unit 10 allows a dentist to quickly move between "cut wet" and "cut dry" functions, or, between other functions which can be achieved with dental control unit 10 without looking away from the work field to activate, deactivate, or preset other switches as has previously been required.

Yet another important feature of the invention is that dental control unit 10 obviates the necessity of having to use a separate three-way syringe to produce air, water, and air-water spray functions. By enabling these easily selected functions to be provided directly from the dental hand piece itself without the drill running, it obviates the need for numerous instrument transfers between the hand piece and the 3-way syringe which are separate instruments.

Still a further important feature of the invention is that it utilizes the ability of an unmodified conventional hand piece to dispense air alone to dry the tooth without the drill running or combined air water spray to wash the tooth without the drill running, as well as to operate a high speed drill in the "cut wet" or "cut dry" functions. The dentist can now easily select and switch between the "cut wet" and "cut dry" functions "on the fly" without stopping the drill rotation. All of the above functions can be selected and accomplished while still using the same four (4) hole input-output tubing as previous foot controls. This facilitates retrofitting the dental control unit 10 to a conventional dental station and unmodified hand piece with no significant changes being needed.

Yet still another important feature of the invention is that the dentist need not look at the dental control unit 10 of the invention to select functions while operating the dental control unit 10 with his foot. The dentist also need not—while working in the mouth of a patient—reposition his body in order to look away from the work field at the dental control unit 10 to select the desired functions of the hand piece.

The following table sets forth the various selectable functional zones that can be activated during use of the dental control unit 10 of the invention, although the order of such zones or the zone(s) used or not used can, as would be appreciated by those of skill in the art, be varied as desired. For example, a zone in which water only is on (and not cooling air or the drill) could be added.

TABLE 1

Valves 51, 52, 53 that are "on" or open, or, "off" or closed when foot control Module 90 is in neutral or is in various selectable functional zones.

| VALVE | ZONE #1 (Drill cuts with water and cooling air) | ZONE #2 (Drill cuts with cooling air only) | NEUTRAL (Drill off, water, and cooling air off) | ZONE #3 (Drill off; cooling air on) | ZONE #4 (Drill off; air-water spray on) |
|---|---|---|---|---|---|
| 51 | OPEN | CLOSED | CLOSED | CLOSED | OPEN |
| 52 | OPEN | OPEN | CLOSED | CLOSED | CLOSED |
| 53 | OPEN | OPEN | CLOSED | OPEN | OPEN |

Notes for Table 1:
(a) In ZONE #2: Foot control module 90 is laterally rotated from neutral to the left.
(b) In ZONE #1: Foot control module 90 is laterally rotated from neutral to the left past ZONE #2 to the end stop.
(c) In ZONE #3: Foot control module 90 is laterally rotated from neutral to the right
(d) In ZONE #4: Foot control module 90 is laterally rotated from neutral to the right past ZONE #3 to the end stop.

In one embodiment of the invention, a dentist acclimates himself or herself to operation of control unit 10 by practicing with his foot (with or without wearing a shoe) laterally moving module 90 (and therefore foot plate 11) through arcs to the left or right of the neutral position until desired selectable functional positions of module 90 are achieved and until the dentist can sense and feel with his foot and leg that such desired selectable functional positions have been achieved. Such positions could, by way of example, be the positions set forth about in Table I.

Having described my invention in such terms as to enable those skilled in the art to understand and practice it, and having described presently preferred embodiments thereof, I claim:

1. In combination with dental apparatus comprising
   a dental high speed hand piece including at least one rotatable drill bit and having at least two operative positions,
   a primary on operative position in which said drill bit is activated and is rotating,
   a secondary off operative position in which said drill bit is deactivated and is stationary,
   at least a first control line to deliver pressurized water to the dental hand piece, at least a second control line to deliver compressed air to the dental hand piece, at least a third control line to activate and deactivate the drill bit, the improvements in the dental apparatus comprising a dental control unit to operate said first, second, and third control lines, said dental control unit comprising (a) a housing positioned on a floor;

(b) a generally horizontally oriented plate pivotally mounted on said housing to be laterally displaceable through an arc by engaging said plate with a foot and pivoting said foot and said plate simultaneously laterally through an arc;

(c) a plurality of horizontally oriented cam edges connected to said plate to move simultaneously with said plate;

(d) a plurality of actuable valves fixedly mounted on said housing and operatively associated with said cam edges and said first, second and third control lines;

said plate and said cam edges being simultaneously displaceable through at least five operative positions to actuate periodically selected ones of said valves, a first operative position in which the drill bit is activated and pressurized water is delivered to said hand piece, a second operative position in which the drill bit is activated and compressed air is delivered to said hand piece, a third operative position in which the drill bit is deactivated, compressed air is not delivered to said hand piece, and pressurized water is not delivered to the hand piece, a fourth operative position in which the drill bit is deactivated and compressed air is delivered to the hand piece, and a fifth operative position in which the drill bit is deactivated and pressurized water and compressed air are delivered to the hand piece.

* * * * *